United States Patent
Josset et al.

(10) Patent No.: US 10,793,682 B2
(45) Date of Patent: Oct. 6, 2020

(54) METHOD FOR MANUFACTURING HYDROPHILIC CELLULOSIC NANOFIBERS IN LOW-POLARITY ENVIRONMENTS AND MATERIALS COMPRISING SUCH NANOFIBERS

(71) Applicant: EMPA Eidgenössische Materialprüfungs- und Forschungsanstalt, Dübendorf (CH)

(72) Inventors: Sébastien Josset, Basel (CH); Philippe Tingaut, Solothurn (CH); Tanja Zimmermann, Gockhausen (CH)

(73) Assignee: EMPA EIDGENÖSSISCHE MATERIALPRÜFUNGS-UND FORSCHNGSANSTALT, Dübendorf (CH)

( * ) Notice: Subject to any disclaimer, the term of this patent is extended or adjusted under 35 U.S.C. 154(b) by 412 days.

(21) Appl. No.: 15/534,276

(22) PCT Filed: Dec. 5, 2014

(86) PCT No.: PCT/EP2014/003264
§ 371 (c)(1),
(2) Date: Jun. 8, 2017

(87) PCT Pub. No.: WO2016/086951
PCT Pub. Date: Jun. 9, 2016

(65) Prior Publication Data
US 2018/0258232 A1  Sep. 13, 2018

(51) Int. Cl.
| | | |
|---|---|---|
| *C08J 3/05* | (2006.01) | |
| *A61K 8/73* | (2006.01) | |
| *C08J 3/09* | (2006.01) | |
| *C08L 1/02* | (2006.01) | |
| *C08B 15/00* | (2006.01) | |
| *A61C 19/00* | (2006.01) | |
| *A61K 8/02* | (2006.01) | |

(52) U.S. Cl.
CPC ............... *C08J 3/05* (2013.01); *A61C 19/00* (2013.01); *A61K 8/027* (2013.01); *A61K 8/731* (2013.01); *C08B 15/00* (2013.01); *C08J 3/09* (2013.01); *C08L 1/02* (2013.01); *A61K 2800/10* (2013.01); *A61K 2800/412* (2013.01); *A61K 2800/48* (2013.01); *C08J 2301/02* (2013.01)

(58) Field of Classification Search
CPC ....... C08J 3/05; C08J 3/09; C08B 15/00; C08L 1/02; A61K 8/731
See application file for complete search history.

(56) References Cited

U.S. PATENT DOCUMENTS

| | | | |
|---|---|---|---|
| 4,341,807 | A | 7/1982 | Turbak et al. |
| 4,481,077 | A | 11/1984 | Herrick |
| 6,057,033 | A | 5/2000 | Bilodeau |
| 6,541,627 | B1 | 4/2003 | Ono et al. |
| 6,967,027 | B1 | 11/2005 | Heux et al. |
| 2005/0048019 | A1 | 3/2005 | Kropke et al. |
| 2015/0093560 | A1 | 4/2015 | Nemoto et al. |

FOREIGN PATENT DOCUMENTS

| | | |
|---|---|---|
| EP | 2 857 583 A1 | 4/2015 |
| WO | 2000/016889 A2 | 3/2000 |
| WO | 2012/038238 A1 | 3/2012 |
| WO | 2012/089929 A1 | 7/2012 |
| WO | 2013/183415 A1 | 12/2013 |

OTHER PUBLICATIONS

International Search Report for corresponding International Application No. PCT/EP2014/003264 dated Aug. 28, 2015.
Written Opinion of the International Searching Authority for corresponding International Application No. PCT/EP2014/003264 dated Aug. 28, 2015.
International Preliminary Report on Patentability for corresponding International Application No. PCT/EP2014/003264 dated Jun. 6, 2017.
Zimmerman et al., "Properties of nanofibrillated cellulose from different raw materials and it reinforcement potential", Carbohydrate Polymers, vol. 79, 2010, pp. 1086-1093.
Tingaut et al., "Synthesis and Characterization of Bionanocomposites with Tunable Properties from Poly(lactic acid) and Acetylated Microfibrillated Cellulose", Biomacromolecules, vol. 11, No. 2, 2010, pp. 454-464.

*Primary Examiner* — Peter D. Mulcahy
(74) *Attorney, Agent, or Firm* — Renner, Otto, Boisselle & Sklar, LLP

(57) ABSTRACT

The present invention relates to a method for manufacturing hydrophilic biopolymers, particularly hydrophilic cellulosic material, particularly cellulose nanofibers like micro- or nanofibrillated cellulose, as described in claim 1; to novel materials comprising hydrophilic biopolymers and to the use of such hydrophilic biopolymers.

12 Claims, 2 Drawing Sheets

Figure 1:
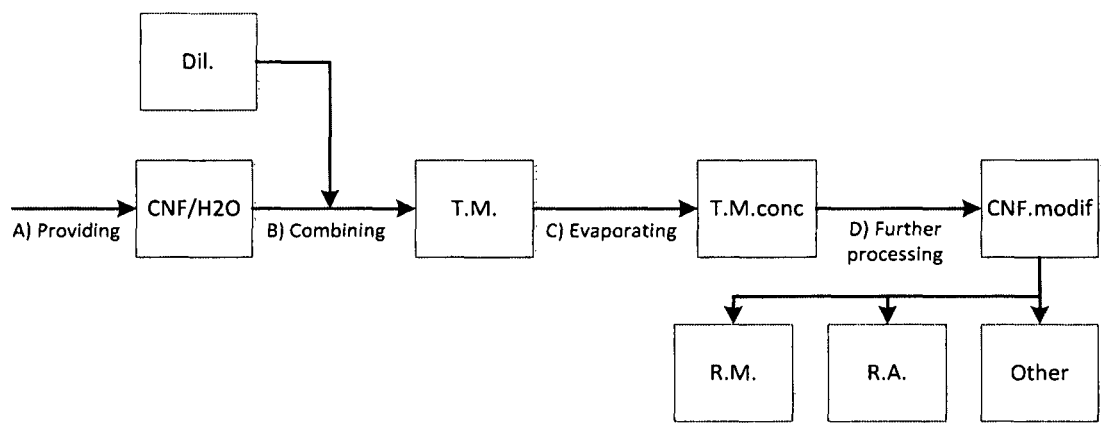

METHOD FOR MANUFACTURING HYDROPHILIC CELLULOSIC NANOFIBERS IN LOW-POLARITY ENVIRONMENTS AND MATERIALS COMPRISING SUCH NANOFIBERS

This application is a national phase of International Application No. PCT/EP2014/003264 filed Dec. 5, 2015 and published in the English language.

The present invention relates to a method for manufacturing hydrophilic biopolymers, particularly hydrophilic cellulosic material containing nanofibers (CNF), to novel materials comprising such CNF and to the use of such CNF.

Hydrophilic biopolymers, particularly hydrophilic cellulose nanofibers (CNF), are an important intermediate in industry, but difficult to handle. Due to their hydrophilic properties, such biopolymers are incompatible with non-polar polymers or solvents. Due to their high water content, chemical modifications of such biopolymers are difficult. Due to their complex chemical structure, such biopolymers are sensitive towards drying, as an irreversible aggregation of the nanofibers occurs (also called hornification), which prevents the redispersion of the dried nanofibers in a diluent. To address these issues, a number of methods have been developed for treating hydrophilic biopolymers in order to subsequently decrease their surface polarity and to enable a homogeneous dispersion in apolar matrices.

Heux et al. (U.S. 69/670,279) discloses a method of manufacturing hydrophilic microfibrillated dispersions of cellulose (MFC) in an organic solvent in the presence of a surfactant. According to this method, specific surfactants are added to an aqueous composition of MFC and the water is removed. The obtained dry product is then re-dispersed in an organic solvent. The presence of surfactants in the final mixture, mandatory according to this document, is considered disadvantageous.

Herrick (U.S. Pat. No. 4,481,077) also discloses a method of manufacturing hydrophilic microfibrillated dispersions of cellulose in an organic solvent in the presence of a surfactant. According to this method, specific surfactants are added to an aqueous composition of never-dried cellulosic pulp and the water is removed. The obtained dry product is then re-dispersed in an organic solvent and micro-fibrillated. Similarly to US '279 above, the presence of surfactants in the final mixture, mandatory according to this document, is considered disadvantageous.

Salminen (WO2012/089929) discloses a method of manufacturing hydrophobic microfibrillated cellulose (MFC) wherein an organic reagent is reacted with the hydroxyl groups on the surface of MFC, characterized by carrying out two successive azeotropic distillations. According to Salminen, an organic solvent (e.g. toluene, benzene, pyridine) in a water suspension of cellulose is used where the reaction with e.g. anhydrides is performed. The first distillation of the ternary mixture of water/MFC/organic solvent aims at reducing the water content of the system, preserving the MFC quality. After reaction with hydrophobization reagents, especially anhydrides, the by-products are removed by a second distillation leading to a binary system hydrophobized MFC/oil that can be mechanically concentrated or dispersed in a low polarity phase. Furthermore, the unavoidable presence of remaining traces of organic solvents is considered disadvantageous and excludes numerous applications.

Tingaut et al. (Biomacromolecules, 2010) describes that dried acetylated MFC can be re-dispersed in apolar matrices/oil through the help of an additional solvent, e.g. chloroform. As such additional solvent has to be removed prior to use, the process is considered disadvantageous.

Thus, it is an object of the present invention to mitigate at least some of these drawbacks of the state of the art.

In particular, it is an aim of the present invention to provide CNF showing none (or reduced) effects of hornification and corresponding methods of manufacturing the same.

These objectives are achieved by the process as defined in claim 1 and by the materials as defined in claims 7 and 8. Further aspects of the invention are disclosed in the specification and independent claims, preferred embodiments are disclosed in the specification and the dependent claims.

The present invention will be described in more detail below. It is understood that the various embodiments, preferences and ranges as provided/disclosed in this specification may be combined at will. Further, depending on the specific embodiment, selected definitions, embodiments or ranges may not apply.

As used herein, the terms "a", "an", "the" and similar terms used in the context of the present invention (especially in the context of the claims) are to be construed to cover both the singular and plural unless otherwise indicated herein or clearly contradicted by the context. As used herein, the terms "including", "containing" and "comprising" are used herein in their open, non-limiting sense. The term "containing" shall include the meaning of "comprising", "essentially consisting of" and "consisting of".

The present invention will be better understood by reference to the figures.

In FIG. 1, a flow chart of the inventive method is shown wherein process steps a) to d) are identified. In this chart "CNF" represents hydrophilic biopolymer (particularly cellulose nanofibers); "Dil" represents the diluent; "H2O" represents an aqueous phase and "T.M." a ternary mixture of "CNF", "Dil" and "H2O"; the indice "conc" denotes the concentrated ternary mixture "CNF/Dil/H2O" in relationship to the water; the indices "modif" relate to the chemically modified CNF; "R.M." represents a rheology modifier, "R.A." a reinforcing agent and "Other" other applications.

Figure 2:
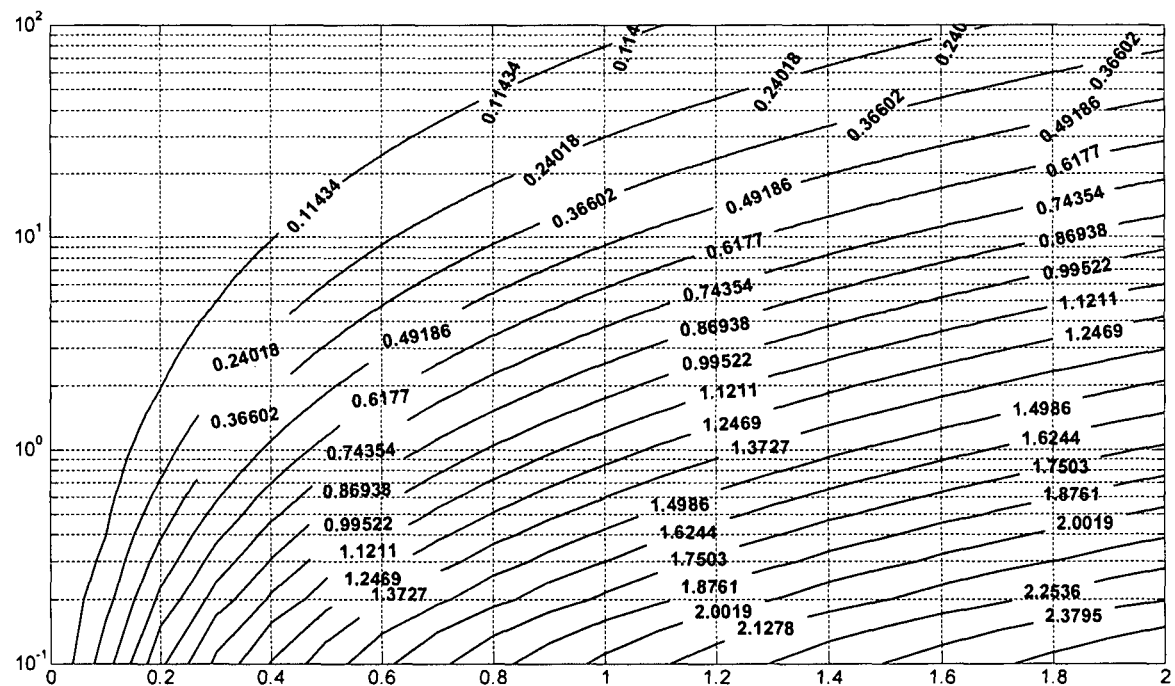

In FIG. 2, the rheological profile of silicon oil containing various amounts of acetylated CNF prepared using mineral oil as diluent is presented (values expressed as the $\log_{10}$ of the viscosity, x-axis: concentration of acetylated CNF in the end product (wt %), y-axis: shear rate (1/s)).

Figure 3:
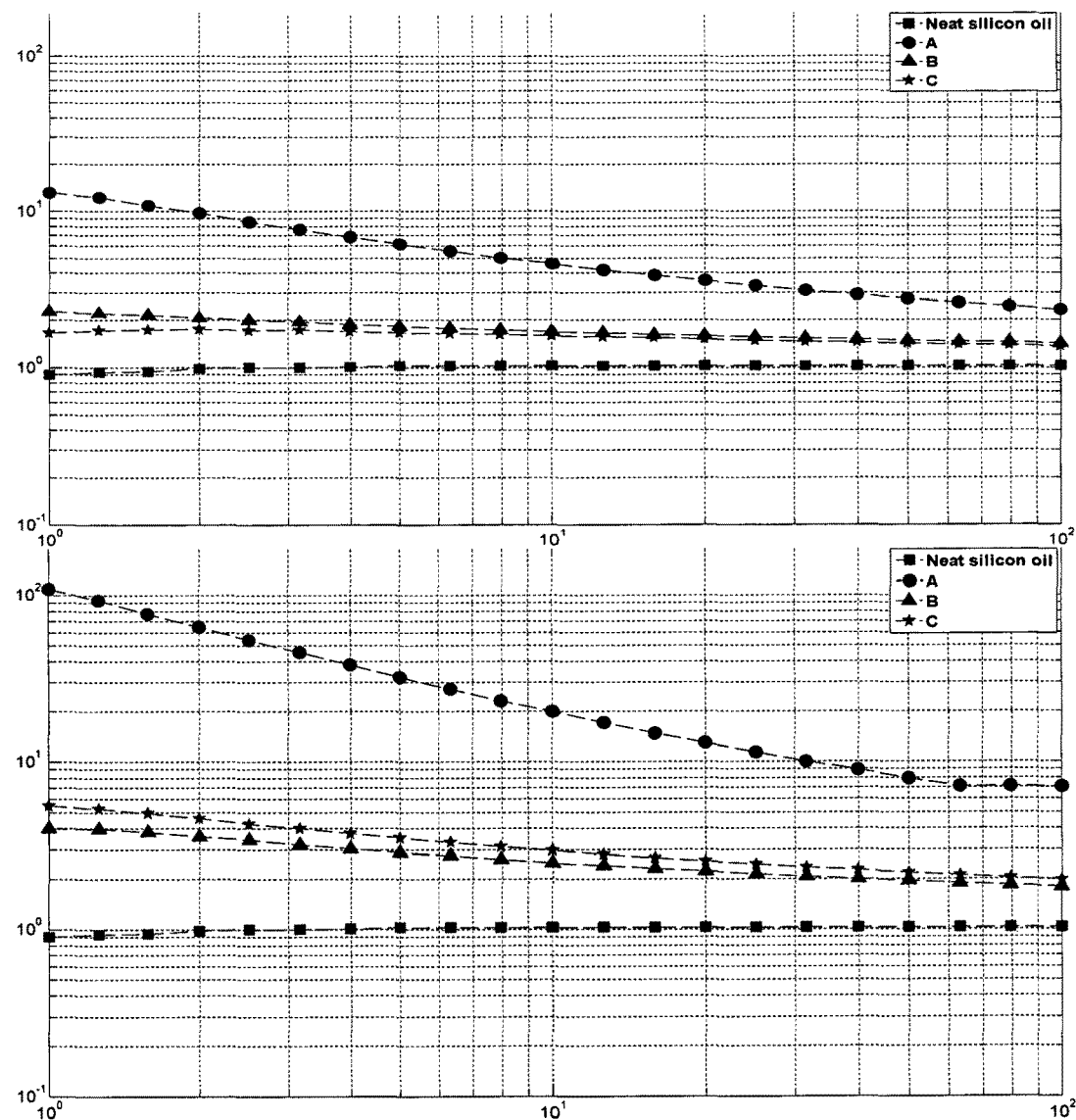

In FIG. 3, the rheological profile of silicon oil containing 2.5 wt. % (top) and 5.0 wt. % (bottom) of acetylated CNF prepared using silicon oil as diluent is presented. The acetylation was conducted at CNF to (water+CNF) ratios of A:68 wt. %, B: 82 wt. % and C: 94 wt. % (y-axis: viscosity (Pa*s), x-axis: shear rate (1/s)).

Figure 4:
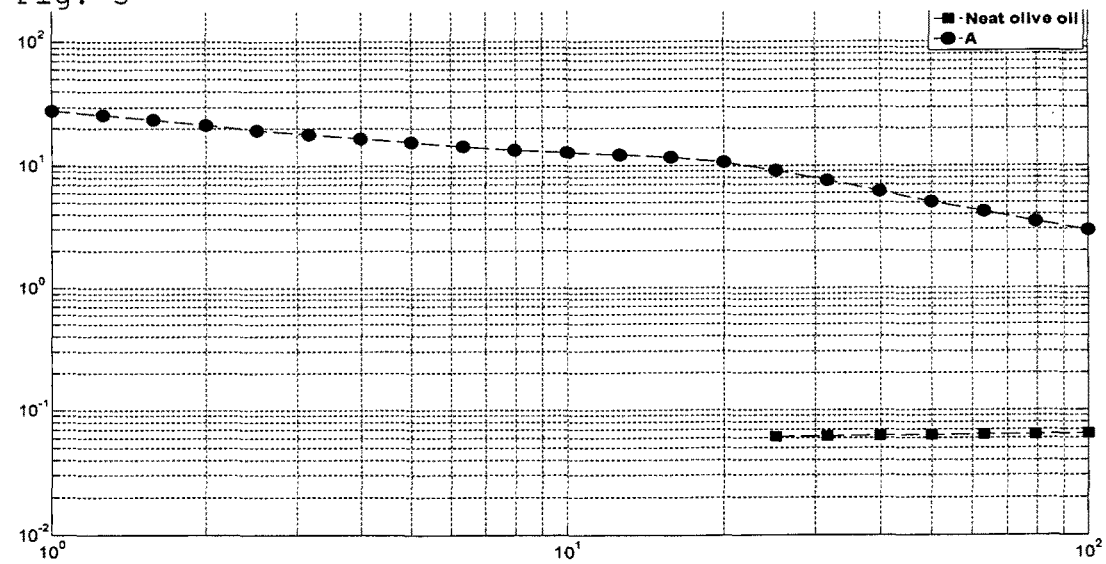

In FIG. 4, the rheological profile of olive oil containing 5.0 wt. % of acetylated CNF prepared using olive oil as diluent is presented. The acetylation was conducted at a CNF to (water+CNF) ratios of A: 50 wt. % (y-axis: viscosity (Pa*s), x-axis: shear rate (1/s)).

In more general terms, in a first aspect, the invention relates to a method for manufacturing hydrophilic biopolymers.

The inventive method comprises the steps of (a) providing an aqueous suspension of said biopolymer; (b) combining said aqueous suspension with a diluent to obtain a ternary system, (c) lowering the water content from said ternary system by evaporation to obtain a suspension of hydrophilic biopolymers in diluent and water; and (d) optionally further processing the obtained suspension.

This process provides a number of advantages when compared to the prior art. First, it is a simple, cost-efficient and environmentally friendly method for obtaining hydrophilic biopolymers. Second, it is a method for obtaining hydrophilic biopolymers with high concentrations in non-polar dispersant and/or diluent (with small amounts of water). Third, it offers a method for efficiently functionalize hydrophilic biopolymers. Fourth, the thus obtained biopolymer shows limited alteration due to hornification. This aspect of the invention shall be explained in further detail below.

Hydrophilic Biopolymers:

A wide range of hydrophilic biopolymers may be used in the inventive process. In the context of this invention hydrophilic biopolymers shall include cellulose nanofibers (CNF), also called e.g. microfibrillated cellulose (MFC), nanofibrillated cellulose (NFC), cellulose nanocrystals or whiskers (depending on the fiber dimensions, aspect ratios and crystallinity).

The process is particularly useful for hydrophilic biopolymers which could be "micro-fibers" or "nanofibers". In the context of the present invention, the fibers have a diameter between 4 nm to 1000 nm and a length of 50 nm to 1 mm; due to their origin, hydrophilic cellulose nanofibers (CNF) contain cellulose as a main component and may additionally contain other polyoses and/or lignin. Typically, the amount of cellulose is more than 90 wt %. The term cellulose as used herein describes the known polysaccharide consisting of a linear chain of several hundred to over ten thousand $\beta(1\rightarrow4)$ linked D-glucose units. The term is understood in its broadest sense, irrespective of its origin, such as plant-derived cellulose, bacteria-derived cellulose (collectively: cellulose of renewable sources) and synthetically obtained cellulose (synthetic cellulose).

In one embodiment, said biopolymer is selected from the group consisting of cellulose, eventually lignin and polysaccharides (e.g. $\beta1\rightarrow3$ glucan, $\beta1\rightarrow3$ xylan, $\beta1\rightarrow4$ mannan) particularly cellulose. The term biopolymer includes natural biopolymers and regenerated biopolymers (i.e., dissolved and precipitated).

A particularly preferred biopolymer is hydrophilic CNF

Step a: Methods to prepare aqueous suspensions of biopolymers are known in the field and described e.g. in Zimmermann et al, Carbohydrate Polymers 2010, 1086-1093 which is incorporated by reference, particularly chapters 2.1-2.3.

The concentration of biopolymer may vary over a broad range and depends on the starting material and the equipment used. Suitable are, for example, 0.1-75% wt % (biopolymer/(biopolymer+water), preferably more than 5 wt %, much preferably more than 40 wt %.

The viscosities of such binary systems may vary over a broad range and include systems of very low viscosity (in the range of water) as well as systems of very high viscosity.

In a preferred embodiment, the suspension is free of surfactants.

Step b: Combining two components, a binary system of step (a) and a diluent, may be accomplished as known in the field. Typically, the binary system of step (a) can be stirred and mixed with the diluent in a reactor before drying. Alternatively, the diluent can be mixed with a pre-concentrated biopolymer (CNF)/water system to produce a high viscosity ternary mixture which can be extruded as a granulate before drying.

The diluent may be chosen from a wide variety of liquids. Advantageously, said diluent being selected from the group of oils (e.g. mineral oils, silicon oils, and natural oils). Advantageously, said diluent has a lower vapour pressure than water at any temperature, for pressures comprised between 0 and 1 atm. Diluent's viscosity may vary over a broad range. In one embodiment, said diluent has a viscosity below 10 Pa·s@20° C., e.g. 1 Pa·s@20° C. This allows for proceeding in a stirred reactor. In case diluents with higher viscosities are used, the drying of the ternary mixtures as granulate is preferred.

In a preferred embodiment, said diluent excludes surfactants. Accordingly, in the context of this invention, fatty acids are not considered surfactants.

In a preferred embodiment, mineral oils are selected such as C12-C30 alkanes, and mixtures thereof. Such mineral oils are commercial items; suitable is Hydroseal (Total).

In a preferred embodiment, silicon oils having a viscosity below 1000 mPa·s are selected. Such silicon oils are commercially available.

In a preferred embodiment, natural oils from plant oils or hydrogenated plant oils are selected. Such plant oils are commercial items or available through known routes. Suitable plant oils are, for example, flax oil and olive oil.

The amount of diluent may vary over a broad range and depends on the overall process (stirred reactor or granulates) and the equipment used. Suitable are, for example, 1 to 5 times the mass of the dry solid content of biopolymer (CNF) suspension to produce granulates, typically 1 to 10 times the volume of aqueous suspension, such as equal volumes.

Step c: This step reduces the water content, or even dries the material. Step c includes any process where water is (partly or fully) evaporated from the mixture due to differences in boiling points, such as distillation, azeotropic distillation, rectification, gaseous flushing (sparging) or stripping. In one embodiment, step c is a distillation under reduced pressure, particularly in the case of a stirred reactor. This embodiment ensures short processing times for step c. In an alternative embodiment, granulates of step b are dried at room temperature and atmospheric pressure using a non-water saturated air stream.

As it becomes apparent, step c excludes extraction and freeze drying.

In an advantageous embodiment, the water content from said ternary system is reduced in step c by evaporation to a value below 30 wt %. In an advantageous embodiment, the water content from said ternary system is reduced in step c by evaporation to a value below 40 wt %. In an advantageous embodiment, the water content from said ternary system is reduced in step c by evaporation to a value below 50 wt %. (In each case based on the ratio: Water/(CNF+Water.)

In an advantageous embodiment, evaporation of step (c) takes place at temperatures between 10° C. and 100° C., but preferably between 50° C. and 80° C. In an advantageous embodiment, evaporation of step (c) takes place at pressures below or equal to the atmospheric pressure.

After performing step c, a ternary phase with lowered amounts of water is obtained, said phase comprising the diluent and dispersed therein the hydrophilic biopolymer. In the case of a stirred reactor, due to the non-miscibility of the biopolymer in the diluent, the biopolymer sediments and can be easily collected. The hydrophilic biopolymer can be obtained in the form of shaped spheres, such as beads in case of a low energy stirring. Depending on the mixing apparatus used and its geometry, different geometries may be obtained; this may be optimized in view of a specific application by routine experiments. This ternary phase with reduced water content is simple to handle; the biopolymers contained therein retain to a large extent their original properties, particularly being re-dispersible. The excess diluent may be filtered out prior further processing steps or the whole system may be directly used in the suspension obtained for further processing.

In the case of the air-dried extrudate, the material keeps its shape and can be further processed as granules.

Accordingly, the invention also relates to a method for manufacturing hydrophilic biopolymers (i) in the form of re-dispersible granulates, and (ii) in the form of a ternary mixture with low water contents.

In one further embodiment, the present invention relates to the process for manufacturing concentrated ternary mixtures with low water contents of micro- or nano-fibrous materials issued from renewable sources, especially cellulose nanofibers, in a diluent.

Step d: As discussed above, the initially obtained suspension may be subject of further processing steps.

In one embodiment, the concentrated spheres of hydrophilic biopolymer are subject to a separation step, i.e. separated from the surrounding diluent phase, e.g. by filtration, centrifugation or sedimentation. When performing the inventive method, the biopolymer is typically obtained in the form of beads and thus simple to separate. The diluent obtained may be recycled, e.g. in step b. The thus obtained biopolymer/may be further processed (i.e., to prepare composites, functionalized to obtain a modified biopolymer water-free, etc . . . ). It was found that the obtained modified biopolymer may be readily re-dispersed in a low-polar or non-polar matrix. Accordingly, the invention also relates to a method for manufacturing a water-free (but not diluent free) material comprising, or essentially consisting of, hydrophilic biopolymer, said method comprising steps a) to c) as described herein, followed by further processing (such as dispersion in other low- or non-polar matrices, functionalization, extrusion, etc. . . . )

In one embodiment, the hydrophilic biopolymer obtained in step c) is subjected to a functionalizing step. Such functionalization is known in the field and typically includes (but not limited to) the conversion of free hydroxyl groups to other functional groups. Such functional groups include but are not limited to esters, aldehydes, ethers, acids, mono, di and tri-alkoxysilanes, etc . . . , classical functional groups in organic and inorganic chemistry which can react with hydroxyl functions. The thus obtained partly or fully modified hydrophilic biopolymers are termed functionalized biopolymers. Accordingly, the invention also relates to a method for manufacturing a functionalized biopolymer comprising steps a) to c) as described herein, followed by chemically modifying the hydrophilic biopolymers obtained in step c) to obtain said functionalized biopolymer.

In one further embodiment, the hydrophilic biopolymer obtained in step c) is subjected to a compounding step. Such compounding step is known in the field and typically includes combination of the suspension of step c) with a (pre-)polymer melt or (pre-)polymer solution to obtain a shaped article comprising a polymer and distributed therein hydrophilic polymer. Accordingly, the invention also relates to a method of manufacturing a polymer blend comprising hydrophilic biopolymer, said method comprising steps a) to c) as described herein, followed by compounding the obtained biopolymers to obtain said polymer blend.

In a second aspect, the invention relates to novel materials of hydrophilic biopolymers. This aspect of the invention shall be explained in further detail below:

In one embodiment, the invention relates to hydrophilic biopolymer, obtained according to a method as described herein. The biopolymer of the present invention distinguishes from known biopolymers as it is re-dispersible. This property is observed even without any chemical modification of the polymer and without addition of further components, such as surfactants. Without being bound to theory, it is believed that the diluent limits the irreversible solidification (e.g. hornification) of the hydrophilic biopolymer by impeaching reactions between adjacent biopolymer chains through its presence, so that the said biopolymer retains its properties. This is a significant difference to the known hydrophilic biopolymers.

In one embodiment, the invention provides for material as described herein, said material being re-dispersible in water.

In one embodiment, the invention provides for a composition containing (i) at least 50 wt % (based on the ratio CNF/(CNF+Water)) hydrophilic biopolymers as described herein, particularly hydrophilic CNF, (ii) at most 50 wt % of water (based on the ratio Water/(CNF+Water)) and (iii) 0,1 to 10 times the volume of the starting CNF suspension in water of diluent. The residual water content may be determined by gravimetry (assuming that the diluent does not evaporate), or by Karl-Fischer-Titration.

It was surprisingly found that the hydrophilic biopolymers of the compositions described herein show very limited hornification since it can be mechanically re-dispersed, even starting from CNF/Water mixtures with high solid contents (e.g. 75%). In the context of the present invention, the term hornification describes the irreversible agglomeration of cellulosic material during drying. Such hornification is explained by the formation of additional hydrogen bonds between amorphous parts of cellulose fibrils during drying. Accordingly, the invention also provides for a composition as described herein not showing or showing very limited hornification.

In a third aspect, the invention relates to the use of hydrophilic biopolymers as described herein. This aspect of the invention shall be explained in further detail below:

Due to its unique properties, particularly for being dispersible in low-polarity matrices, the materials as described herein may be subject to a great variety of industrial applications.

In one embodiment, the invention provides for the use of a material as described herein in cosmetic applications.

In one embodiment, the invention provides for the use of a material as described herein as food additive.

In one embodiment, the invention provides for the use of a material as described herein in building technologies (such as silicon sealants, etc. . . . ), lubricants, paints and surface treatments of organic (such as wood) and inorganic materials.

To further illustrate the invention, the following examples are provided. These examples are provided with no intend to limit the scope of the invention.

Example I: Water Content Reduction Through Evaporation Using Distillation Under Reduced Pressure in Mineral Oil, Acetylation and Use as a Rheology Modifier in Silicon Oil Synthesis:

Step a) A suspension comprising 20 g CNF and 180 g water (i.e. 10 wt. %. solid content) was prepared according to Zimmermann et al. (Carbohydrate Polymers, 2010. 79(4): p. 1086-1093).

Step b) To the above suspension, 200 mL of Mineral Oil (10 mPa*s @20° C.) was added upon vigorous stirring.

Step c) The obtained ternary phase was subjected to distillation (400 mbar, 70° C.), while vigorously stirring until the remaining water content, as determined by Karl-Fischer Titration was 50%. This resulted in a suspension comprising CNF beads with a diameter of approx. 1 to 5 mm dispersed in a clear phase of mineral oil.

Step d) The material was subjected to an acylation reaction. The material obtained in step c) above was combined with 200 mL acetic anhydride and reacted @70° C. overnight. Acetic acid and excess anhydride were removed at this temperature/400 mbar. The obtained solid material (acetylated CNF) with mineral oil was recovered through filtration. The acetylated CNF content was measured by gravimetry after 3 successive washing steps of the material with chloroform to remove the oil and estimate the CNF content (25 wt %).

Step e) This acetylated CNF in mineral oil was used as a rheology modifier for silicon oil (viscosity: 1000 mPa*s @20° C. @0.1/s). To this purpose, different amounts of the binary mixture were dispersed in the silicon oil and the viscosity of the resulting ternary mixture was evaluated at different shear stresses (FIG. 2).

Example II: Water Content Reduction Through Evaporation at Normal Temperature and Pressure in Silicon Oil, Acetylation and Use as a Rheology Modifier in Silicon Oil Step a) A suspension comprising 234 g CNF and 1766 g water was prepared according to Zimmermann et al (Carbohydrate Polymers, 2010. 79(4): p. 1086-1093).

Step b) To the above suspension, 400 mL of Silicon Oil (1000 mPa*s @20° C. @0.1/s) was added upon vigorous stirring to form a concentrated suspension which did not show de-mixing. This material was extruded into 5 mm pellets (diameter) before processing.

Step c) The pellets were allowed to dry through evaporation under controlled atmosphere (20° C. and relative humidity comprised between 70 and 80%). The water content of the material was estimated through gravimetry and samples (50 g of ternary mixtures) were taken at CNF to (water+CNF) ratios of A: 68 wt. %, B: 82 wt. % and C: 94 wt. %. This last value was confirmed through six Karl-Fischer titrations.

Step d) The samples were subjected to an acetylation reaction. The materials obtained in step c) above were combined with 200 mL acetic anhydride and reacted @70° C. overnight. Acetic acid and excess anhydride were removed through filtration and subsequent evaporation under ambient air. The mass ratio acetylated CNF to oil was measured by gravimetry after 3 successive washing steps of the material with chloroform. The acetylated materials were dried overnight at 105° C. and the degree of acetylation was evaluated with infrared spectroscopy, by calculating the peak height ratio of the carbonyl band at 1730 cm$^{-1}$ to the cellulose band at 1060 cm$^{-1}$ and subsequently calculating the acetyl content (Ac %) using a calibration curve (Tingaut, P., Zimmermann, T., Lopez-Suevos, F. Biomacromolecules, 2010, 11, 454-464). The % Ac values calculated for the three samples were (averaged on three measurements): A: 10.76%, B: 17.45%, C: 18.47%.

Step e) This acetylated materials containing silicon oil were used as a rheology modifier for silicon oil (viscosity: 1000 mPa*s @20° C. @0.1/s). To this purpose different amounts of the binary mixtures were dispersed in the silicon oil at 2.5 wt. % and 5.0 wt. % of acetylated fibers in the end mixture. The viscosities of these resulting binary mixtures were evaluated at different shear stresses (FIG. 3).

A negative control involving the concentration through the same procedure was performed on CNF without oil (up to a ratio CNF/(Water+CNF) of 60 wt. %). The acetylation of 50 g of this material with 200 mL of acetic anhydride was performed. After the removal of the unreacted anhydride and the acetic acid, this material could not be dispersed in the silicon oil properly enough to be able to measure the viscosity due to the presence of numerous large and solid particles.

Example III: Water Content Reduction Through Evaporation at Normal Temperature and Pressure in Olive Oil, Acetylation and Use as a Rheology Modifier in Olive Oil Step a) A mixture comprising 20 g CNF and 20 g water was prepared according to Zimmermann et al (Carbohydrate Polymers, 2010. 79(4): p. 1086-1093) followed by a mechanical treatment to increase the solid content.

Step b) The above system was blended with 200 mL of olive oil (<0.1 Pa*s @20° C. @0.1/s).

Step c) The ternary mixture was heated up to 70° C. with continuous stirring until the ratio CNF/(CNF+water) reached 75 wt. % (gravimetric determination).

Step d) The samples were subjected to an acetylation reaction. The materials obtained in step c) above were combined with 100 mL acetic anhydride and reacted @70° C. overnight. Acetic acid, excess anhydride and excess oil were removed through filtration and subsequent evaporation under ambient air. The mass ratio acetylated CNF to oil was measured by gravimetry after 3 successive washing steps of the material with chloroform.

Step e) These acetylated materials containing olive oil were used as a rheology modifier for olive oil (viscosity<0.1 Pa*s @20° C. @0.1/s). The viscosity of the resulting binary mixtures was evaluated at different shear stresses (FIG. 4).

Example IV: Use of the Acetylated CNF as a Reinforcing Agent

Synthesis:

The step a) to d) are similar to those of the example II and the material used in this example corresponds to the one issued from the acetylation of the ternary mixture (silicon oil-CNF-water).

step e) This acetylated materials with an acetyl content (Ac %) of 10.8% containing 60 wt. % silicon oil were used as a reinforcement in a cross-linked silicon based composite. 28 g PDMS (Mn~80000 g/mol) and 12 g PDMS (Mn~550 g/mol) were introduced in a 150 mL PE cup and mixed with a mechanical stirrer for 5 min at room temperature. Then, 0.5 g of the acetylated CNF containing oil were homogenized in the former mixture with a high-speed mixer at 11000 rpm for 5 min. 3.5 g tetrapropylorthosilicate (TPOS) and 0.26 g tin(II) 2-ethylhexanoate were then added under stirring and the suspension was cooled down to 2° C. After the final mixture was stirred for 2 min, composite films were obtained by casting 20 g of the suspension in a Polypropylene (PP) mould and applying a vacuum treatment to remove any air bubble. Two films (Length: 110 mm, width: 36 mm, thickness: 1.70 mm) were obtained and dried at room temperature in a fumed hood for 72 h. Two reference silicon films were prepared using the same protocol without acetylated materials. The mechanical properties of the reference material and its composites were evaluated in static tension mode using a Zwick Z010/TH2A (Zwick GmbH & Co. KG, Ulm, Germany). The pre-load applied was 0.1 N, the loading speed 100 mm/min. The Young's modulus (E), Tensile strength (σ at Fmax) and elongation to break (ε at Fmax) were obtained from each stress-strain curve. The results presented are the mean values and the standard deviation of at least 12 measurements (Table 1).

TABLE 1

4 Table presenting the E modulus, tensile strength (σ at Fmax) and elongation at break (ε at Fmax) of a silicon film and its composite reinforced with 1 wt % of acetylated CNF.

|  | E modulus (MPa) | σ at Fmax (MPa) | ε at Fmax (%) |
|---|---|---|---|
| Silicon film | 2.13 ± 0.42 | 0.33 ± 0.06 | 24.30 ± 5.97 |
| Silicon film + 1 wt % acetylated CNF | 2.17 ± 0.25 | 0.97 ± 0.23 | 66.98 ± 5.02 |

The tensile strength of the silicone is increased by 293% after the incorporation of acetylated CNF.

The invention claimed is:

1. A method for manufacturing hydrophilic nanofibrous biopolymers comprising the steps of
   (a) providing an aqueous suspension of said biopolymer;
   (b) combining said aqueous suspension with a diluent to obtain a ternary system,
   said diluent being selected from the group consisting of mineral oils, silicon oils, natural oils,
   said diluent having a lower vapour pressure than water (for temperatures between 0-100° C. and pressures between 0-1 atm);
   (c) reducing the water content from said ternary system by evaporation below 30 wt %;
   (d) optionally further processing the obtained suspension of hydrophilic biopolymers in diluent;
   and wherein said aqueous suspension and said diluent are free of surfactants.

2. The method of claim 1 wherein the suspension of step (a) has a concentration of biopolymer in the range of 0.1-75 wt %.

3. The method of claim 1 wherein the amount of diluent in the ternary system of step (b) is in the range of 1/10 to 10 (v/v) fold the amount of aqueous phase.

4. The method of claim 1 wherein the water content reduction is achieved by evaporation of step (c) at temperatures between 10° C. and 100° C. and pressures below or equal to the atmospheric pressure.

5. The method of claim 1, wherein said step (d) comprises
   the obtaining of a ternary mixture (biopolymer-water-diluent) with reduced water content; and/or
   functionalizing the biopolymers to obtain a functionalized biopolymer; and/or
   compounding the obtained biopolymers to obtain a polymer blend comprising said hydrophilic biopolymer.

6. A hydrophilic biopolymer, obtained according to a method of claim 1.

7. A composition consisting of:
   more than 50 wt % (CNF/(Water+CNF)) and up to 100 wt % (CNF/(Water+CNF)) hydrophilic cellulose nanofibers (CNF),
   at most 50 wt % (Water/(Water+CNF)) water,
   between 0.1 to 10 times the volume of the starting binary mixture CNF in water of diluents selected from the group consisting of mineral oils, silicon oils, natural oils;
   wherein said composition being dispersible; and wherein said composition being solid or semi-solid.

8. The composition of claim 7 being free of, or essentially free of, other diluents.

9. The composition of claim 7 being dispersible in low polar materials.

10. A method of using a composition according to claim 7 (a) as rheology modifier in cosmetic applications, (b) as additive in food and paints, (c) as reinforcing material in building technologies, (d) as lubricant, (e) as surface treatments of organic or inorganic materials.

11. The method of claim 1, wherein the hydrophilic nanofibrous biopolymers are hydrophilic cellulose nanofibers (CNF).

12. The hydrophilic biopolymer of claim 6, wherein the hydrophilic biopolymer is selected from hydrophilic microfibrillated dispersions of cellulose (MFC) and hydrophilic cellulose nanofibers (CNF).

* * * * *